United States Patent [19]

Suzuki

[11] Patent Number: 4,753,761
[45] Date of Patent: Jun. 28, 1988

[54] METHOD FOR PRODUCTION OF EXPANSIBLE MACROMOLECULAR MATERIAL AND POROUS MACROMOLECULAR MEMBRANE

[75] Inventor: Makoto Suzuki, Ibaraki, Japan

[73] Assignees: Agency of Industrial Science & Technology; Ministry of International Trade & Industry, both of Tokyo, Japan

[21] Appl. No.: 102,853

[22] Filed: Sep. 30, 1987

Related U.S. Application Data

[62] Division of Ser. No. 31,675, Mar. 30, 1987, Pat. No. 4,717,800.

[30] Foreign Application Priority Data

Nov. 10, 1986 [JP] Japan .................................. 61-268019

[51] Int. Cl.[4] .......................... B05B 3/00; B29C 35/02
[52] U.S. Cl. ........................................ 264/28; 264/49; 264/234; 264/288.8; 264/289.6; 521/64; 521/141; 210/500.42
[58] Field of Search ...................... 264/49, 234, 288.8, 264/289.6, 28; 521/64, 141

[56] References Cited

U.S. PATENT DOCUMENTS

| | | | |
|---|---|---|---|
| 3,876,581 | 4/1975 | Neogi | 521/62 |
| 4,083,906 | 4/1978 | Schindler et al. | 521/62 |
| 4,109,066 | 8/1978 | Dick et al. | 521/62 |
| 4,401,790 | 8/1983 | Ter Jung et al. | 521/62 |

Primary Examiner—Morton Foelak
Attorney, Agent, or Firm—Oblon, Fisher, Spivak, McClelland & Maier

[57] ABSTRACT

An expansible macromolecular material is produced by a method which comprises mixing an aqueous polyvinyl alcohol solution, an acidic aqueous macromolecular electrolyte solution, and a basic aqueous macromolecular electrolyte solution thereby preparing a composite polymer and subjecting this composite polymer to at least one cycle of alternate freezing and defrosting treatments. A macromolecular membrane constituted of said expansible macromolecular material and containing numerous through holes is obtained by mixing, freezing, and defrosting the aforementioned three mixed aqueous solutions under specific conditions.

6 Claims, 4 Drawing Sheets

METHOD FOR PRODUCTION OF EXPANSIBLE MACROMOLECULAR MATERIAL AND POROUS MACROMOLECULAR MEMBRANE

This is a divison, of application Ser. No. 07/031,675, filed Mar. 30, 1987, now U.S. Pat. No. 4,717,800.

FIELD OF THE INVENTION AND RELATED ART STATEMENT

This invention relates to a reversibly expansible macromolecular material usable as artificial muscles and as drive sources for robots, artificial limbs, medical welfare devices, etc., to a method for the production of the macromolecular material, and to a porous macromolecular membrane using the macromolecular material.

The term "reversibly expansible macromolecular material" as used herein means a substance which, like rubber, expands or contracts on exposure to tensile force or compressive force and restores to the original shape on release of the force. Among the substances of this nature are included those which shrink or inflate by reversibly changing their shape or structure, depending on changes in chemical environmental conditions such as, for example, pH (concentration of hydrogen ion). These substances not merely possess elasticity and strength but also exhibit an ability to convert such chemical energies as pH to mechanical work. Thus, they are known to be useful as so-called mechanochemical actuators, i.e. drive sources which are actuated by such chemical signals as pH.

As techniques for producing mechanochemical macromolecular materials which are usable as main components for the mechnochemical actuators, the synthetic method which involves reaction of a plurality of polymers under conditions of high temperature and pressure and the method of radical polymerization have been known to the art.

The former method is disclosed in W. Kuhn, Angew Chem., 70, 58 (1958) and the latter method in Japanese Patent publication SHO No. 60(1985)-68087 (Japanese Patent Public Disclosure SHO No. 61(1986)-228009) titled "Method for production of reversibly expansible macromolecular membrane" and filed by the same applicant.

The former method has the following disadvantage. Despite the advantage that the cross-linking for the synthesis is effected by a heat treatment and, therefore, is obtained uniformly, this method is inferior to the freezing-defrosting method in the ability to produce a material capable of quick response. Specifically, the response of the product of this method is inevitably slow because the product does not form a micron-order reticular structure which permits quick permeation of a solution.

The latter method produces the macromolecular material by radical polymerization using methacrylic acid and bis-acrylamide, for example. The macromolecular material produced by this method shrinks and resists tension when the pH of the environment is low (acidic) and inflates and yields to tension when the pH is high (alkaline). In the contract state, the material withstands a tensile force of 1 to several $kg/cm^2$, whereas in the elongated condition, the material breaks under a tensile force of some hundreds of $g/cm^2$.

The speed of the response, i.e. the speed at which the macromolecular material expands or shrinks in response to the change in the environment, is low. Thus, the macromolecular material produced by the latter method leaves much to be desired as regards practicality.

In the circumstances, the desirability of developing a mechanochemical macromolecular material capable of withstanding still higher tensile force and making quick response and, therefore, usable in robots, medical welfare devices, artificial limbs, etc. has found growing recognition.

Some of the mechanochemical macromolecular materials heretofore known to the art shrink in an acidic environment and inflate in an alkaline or neutral environment and others shrink in an alkaline environment and inflate in an acidic or neutral environment. Thus, all of them shrink and resist tension in an acidic or alkaline environment and inflate and yield to tension in a neutral environment.

The term "inflation" as used here means the increase of volume due to counter ion pressure, while the term "shrinkage" as used here means the phenomenon that the polymer such as, for example, polyvinyl alcohol which forms the main reticular structure restores to its original volume from the inflated set not by counter ion pressure but by the elasticity originating in the reticular structure. It, in effect, means the situation in which the material elongated and caused to assume a volume larger than the standard volume is allowed to restore to the standard volume. Thus, in the prior art this shrinkage is different from an active shrinkage caused by a counter ion pressure.

OBJECT AND SUMMARY OF THE INVENTION

An object of this invention is to provide (1) a method of production of an expansible molecular material having a high response speed and possessing a tensile strength of not less than 5 $kg/cm^2$, the expansible molecular material exhibiting a characteristic quality of producing expansion and contraction by the counter ion pressure owing to change of pH, i.e. of inflating in an acidic and alkaline environments and shrinking in a neutral environment;

(2) an expansible macromolecular material; and (3) a porous macromolecular membrane formed of the macromolecular material.

These macromolecular material and porous macromolecular membrane are suitable as materials for mechanochemical actuators and are capable of forming various mechanochemical automatic control circuits.

To accomplish the object described above according to the present invention, there are provided a method for the production of a reversibly expansible macromolecular material, which comprises mixing an aqueous solution of containing 10 to 50 wt. % of a polyvinyl alcohol having a molecular weight of at least 30,000 with an acidic macromolecular electrolyte and a basic macromolecular electrolyte each having a molecular weight of at least 50,000 in amounts such that the molar ratio of the polyvinyl alcohol to either of the acidic and basic macromolecular electrolytes falls in the range of (10~3):(2~1) thereby forming a composite polymer and subjecting the composite polymer to between 1 and 20 cycles of alternate freezing and defrosting treatments, the freezing treatment being effected at a temperature in the range of −10° C. to −200° C. and the defrosting treatment being effected at normal room temperature; a method for the production of a reversibly expansible macromolecular material, which comprises a step of mixing an aqueous solution of 5 to 30 wt.

% of a polyvinyl alcohol having a molecular weight of at least 70,000 and a saponification degree of at least 98% with at least one member selected from the group consisitng of an aqueous solution of 10 to 50 wt. % of an acidic macromolecular electrolyte having a molecular weight of at least 50,000 and an aqueous solution of 10 to 50 wt. % of a basic macromolecular electrolyte having a molecular weight of at least 50,000 in amounts such that the molar ratio of the polyvinyl alcohol to either of the acidic macromolecular electrolyte and basic macromolecular electrolyte falls in the range of (10~3):(2~1) thereby forming a composite polymer, a step of subjecting the composite polymer to between 1 and 20 cycles of alternate freezing and defrosting treatments, the freezing treatment being effected at a temperature in the range of $-10°$ C. to $-200°$ C. and the defrosting treatment being effected at normal room temperature, a step of elongating said composite polymer, a step of subjecting said elongated composite polymer to between 1 and 20 cycles of sequential treatments of elongation, freezing in an elongated state at a temperature in the range of $-15°$ C. to $-200°$ C., and defrosting at normal room temperature while maintaining the elongated state, and a step of drying the composite polyer in a draft; a reversibly expansible macromolecular material obtained by mixing an aqueous solution of 10 to 50 wt. % of a polyvinyl alcohol having a molecular weight of at least 30,000 with at least one member selected from the group consisting of an aqueous solution of 10 to 50 wt. % of an acidic macromolecular electrolyte having a molecular weight of at least 50,000 and an aqueous solution of 10 to 50 wt. % of a basic macromolecular electrolyte having a molecular weight of at least 50,000 and subjecting the resulting mixture to between 1 and 20 cycles of alternate freezing and defrosting treatments, the freezing treatment being effected at a temperature in the range of $-10°$ C. to $-200°$ C. and the defrosting treatment being effected at normal room temperature; and a porous macromolecular membrane formed of a reversibly expansible macromolecular material obtained by mixing an aqueous solution of 10 to 50 wt. % of a polyvinyl alcohol having a molecular weight of at least 30,000 with at least one member selected from the group consisting of an aqueous solution of 10 to 50 wt. % of an acidic macromolecular electrolyte having a molecular weight of at least 50,000 and an aqueous solution of 10 to 50 wt. % of a basic macromolecular electrolyte having a molecular weight of at least 50,000 and subjecting the resulting mixture to between 1 and 20 cycles of alternate freezing and defrosting treatments, the freezing treatment being effected at a temperature in the range of $-10°$ C. to $-200°$ C. and the defrosting treatment being effected at normal temperature, and the porous macromolecular membrane and possessing a thickness in the range of 10 to 500 $\mu$m and containing numerous through holes of a diameter in the range of 2 to 50 $\mu$m.

DETAILED DESCRIPTION OF THE PREFERRED EMBODIMENT

Figure 1:
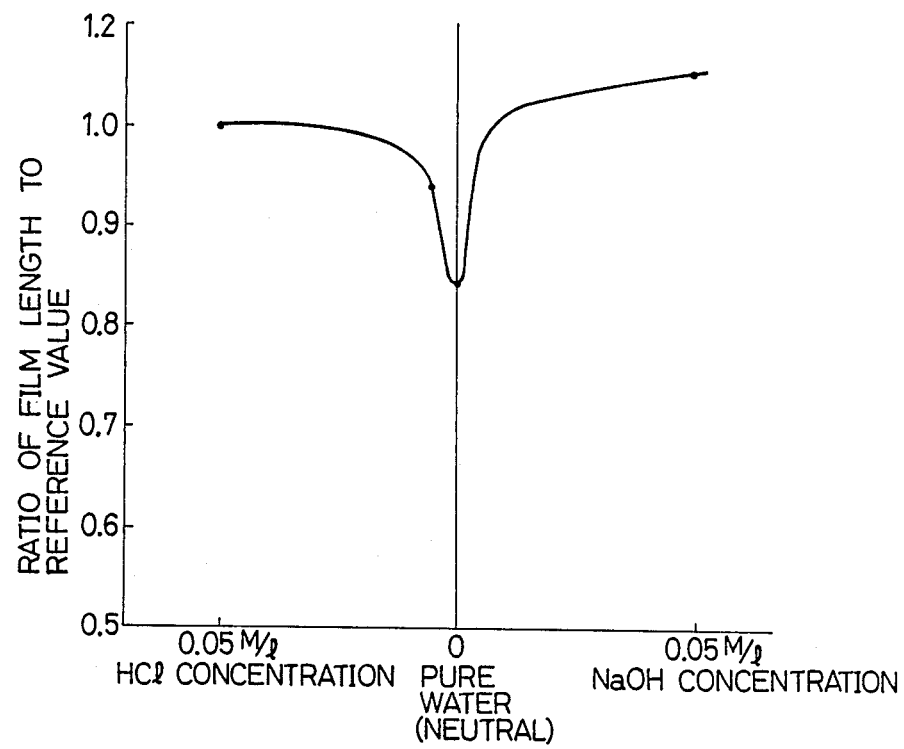
FIG. 1 is a diagram showing the relation between the change in length and the environment obtained of an expansible macromolecular material produced in Example 1.

Concrete examples of the acidic macromolecular electrolyte usable in the present invention include polyacrylic acid, polymethacrylic acid, and other similar polyacids. Other macromolecular electrolytes such as carboxylic acids and derivatives thereof which possess similar properties are also usable. Concrete examples of the basic macromolecular electrolytes include polyallyl amine, polyvinyl amine, polyamino styrene and other primary amines. Other basic macromolecular electrolytes which possess similar properties as those enumerated above are also usable.

By the method of this invention for the production of an expansible macromolecular material, there is first obtained a composite polymer wherein a polyvinyl alcohol having a high molecular weight forms a main reticular structure and an acidic macromolecular electrolyte such as polyacrylic acid and a basic macromolecular electrolyte such as polyallyl amine are intermingled in the interstices of the reticular structure. The aqueous solution of polyvinyl alcohol is disposed to form a hydrogel by a strong hydrogen bond at low tempertures. The other components of the mixed material contribute to the formation of the composite polymer in state intertwined with the polyvinyl alcohol. Since this hydrogen bond occurs in the composite polymer which has been subjected to one or more cycles of freezing and defrosting treatments and has therefore assumed the state of a high-density hydrogel exhibiting high strength throughout, the produced composite polymer acquires strength of a magnitude more than ten times the strength of the conventional "mechanochemical macromolecular material" mentioned above, withstands tension of at least 5 kg/cm$^2$, preferably 10 kg/cm$^2$, can respond quickly to pH change and is usable as a material for mechanochemical actuators. Further, as demonstrated in the working examples to be described later and illustrated in the accompanying drawings, the macromolecular material shrinks in a neutral environment and this shrinkage is an active shrinkage due to the counter ion pressure which originates in the positive and negative ions generated during the electrolysis caused by the electrolyte in the solution. Moreover, since this macromolecular material is a rubber elastomer, it has a satisfactory mechanical affinity for the jig to be used in fixing the material in place and, therefore, enjoys a salient feature that it is not susceptible to easy breakage due to concentration of stress during elongation and contraction.

It is particularly noteworthy that while the conventional mechanochemical material has a rather low speed of response taking not less than 1 minute to expand or contract at the exchange of solutions where the material has a wall thickness of 100 $\mu$m, for example, the expansible macromolecular material obtained in the same wall thickness by this invention responds in a matter of 5 to 10 seconds. The speed is twice as high where the exchange is between water and acetone.

This high speed of response made by the macromolecular material is demonstrated in the working examples cited later.

The present invention further embraces a porous macromolecular membrane possessing a thickness in the range of 10 to 500 μm and containing numerous holes formed in the direction of thickness in a diameter of 2 to 50 μm, which porous macromolecular membrane is formed of a reversibly expansible macromolecular material (hereinafter referred to as "material for porous macromolecular membrane") obtained by mixing an aqueous solution of 10 to 50 wt. % of a polyvinyl alcohol having a molecular weight of at least 30,000 with at least one member selected from the group consisting of an aqueous solution of 10 to 50 wt. % of an acidic macromolecular electrolyte having a molecular weight of at least 50,000 and an aqueous solution of 10 to 50 wt. % of a basic macromolecular electrolyte having a molecular weight of at least 50,000 and subjecting the resulting mixture to between 1 and 20 cycles of alternate freezing and defrosting treatments, the freezing treatment effected at a temperature in the range of $-10°$ C. to $-200°$ C. and the defrosting treatment at normal room temperature.

As compared with the shrinkable macromolecular material obtained by mixing a polyvinyl alcohol and acidic and basic electrolytes and then simply freezing and defrosting the resulting mixture, the porous macromolecular membrane mentioned above permits quick permeation of a solvent. This fact clearly indicates that this porous macromolecular membrane, when used as an actuator, acquires a property of quickly responding to an expanding or contracting motion.

When a plurality of such porous macromolecular membranes are superposed to serve as an actuator and are brought into contact with a solvent, the resulting laminate actuator satisfactorily retains the high permeability because the solvent successively passes through the through holes in the component membranes. Since the component membranes quickly expand and contract in response to changes in the condition of the solvent, the actuator produced by the union of the component membranes enjoys an excellent presponse property. Further, since the chain structures of polymer in the porous macromolecular material are not severed during the formation of through holes, the tensile strength of the porous macromolecular material is not degraded by the formation of the through holes.

During the exchange of solvents, the porous macromolecular membrane can respond in a matter of about 1 second because the membrane permits one solvent lodged previously therein to be forced out quickly through the through holes and the membrane, immediately after immersion in the other solvent, permits immediate permeation by the other solvent. Thus, this membrane has a decisively short response time as compared with the conventional countertype. The polyvinyl alcohol, acidic macromolecular electrolyte, and the basic macromolecular electrolyte which are the components of the porous macromolecular membrane are desired to possess molecular weights of at least 70,000, 170,000, and 60,000 and contain functional groups in a molar ratio of 1:0.1~0.25:0.1~0.25.

Now, the present invention will be described more specifically below with reference to working examples.

EXAMPLE 1

An aqueous solution of 19% by weight of a polyvinyl alcohol having a molecular weight of about 40,000, an aqueous solution of 29% by weight of polyacrylic acid having a molecular weight of about 170,000, and an aqueous solution of 23% by weight of polyallyl amine having a molecular weight of about 60,000 were mixed in a molar ratio of 5:1:1 to give rise to a composite polymer. This composite polymer was subjected ten cycles of alternate freezing and defrosting treatments, the freezing treatment being effected by 2 hours' standing in an environment of $-15°$ C. and the defrosting treatment being effected by 2 hours' standing at normal room temperature, to afford an expansible macromolecular material. This material was tested for change of length under various environments. The relation between the change in length and the environment was as shown in FIG. 1. As will be noted from FIG. 1, based on the length in the acidic and alkaline environment taken as 1, this material assumed a length of about 0.85 in pure water. The tension of this macromolecular material was not less than 5 kg/cm$^2$.

Then, the macromolecular material obtained in this example was tested for response speed, i.e. the length of time actually required by this material to show a change in length in response to a change in the environment. the method employed for the determination of this response time was as follows.

Three samples of the material were prepared, held under different tensions of 100 g/cm$^2$, 200 g/cm$^2$, and 300 g/cm$^2$, and tested for changes in length relative to elapse of time.

A given membrane 100 μm in thickness, 1 cm in width, and 5 cm in length was set in place with the opposite ends thereof nipped fast with plastic jigs. One of the jigs was fixed on the bottom of a cylindrical glass container and the other jig fastened to a hook. This hook was secured to one end of a balancing bar. A weight was suspended from the other end of the balancing bar opposed to the first end across the fulcrum of the balancing bar so as to exert tension upon the film. Then, the movement of the balancing bar produced when the cylindrical container was filled with an alkaline solution was measured. Subsequently, the movement of the balancing bar produced when the cylindrical container was filled with alcohol in place of the alkaline solution was similarly measured. the change in length of the membrane was determined from the two movements of the balancing bar.

Figure 2:
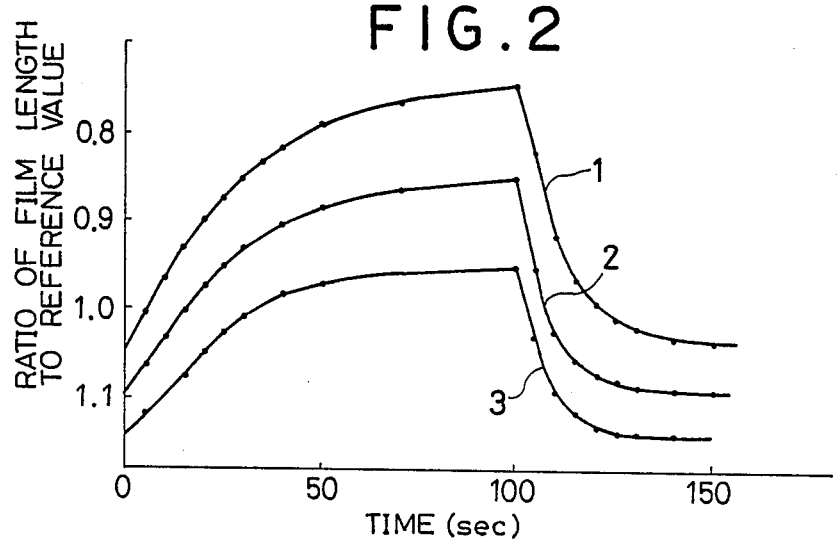
FIG. 2 is a diagram showing the speed of response of the expansible macromolecular material produced in Example 1.

The results of the test were as shown in FIG. 2.

In the graph of FIG. 2, the curves 1, 2 and 3 represent changes in length of membrane based on reference value along the course of time under tensions of 100 g/cm$^2$, 200 g/cm$^2$, and 300 g/cm$^2$, respectively. It will be noted from the graph that changes from the reference value were abrupt after elapse of about 100 seconds.

EXAMPLE 2

A composite polymer obtained by mixing an aqueous solution of 19% by weight of a polyvinyl alcohol having a molecular weight of about 70,000 and a saponification degree of 99.5%, an aqueous solution of 29% by weight of polyacrylic acid having a molecular weight of about 170,000, and an aqueous solution of 23% by weight of polyallyl amine having a molecular weight of about 60,000 at a molar ratio of 6:1:1 was applied in a thickness of 10 to 500 μm on a flat glass plate and subjected to ten cycles of alternate freezing and defrosting treatments, the freezing treatment being effected by 15 minutes' standing in an environment at −50° C. and the defrosting treatment being effected by 15 minutes' standing at normal room temperature, to give rise to a membrane. The membrane was then monoaxially or biaxially stretched on the flat plate in air or nitrogen so that it would not undergo shrinkage, subjected once up to 20 to the aforementioned cycles of freezing and defrosting treatments, and finally dried in a draft, to produce a shrinkable macromolecular material. This material withstood tension exceeding 5 kg/cm$^2$.

Figure 3:
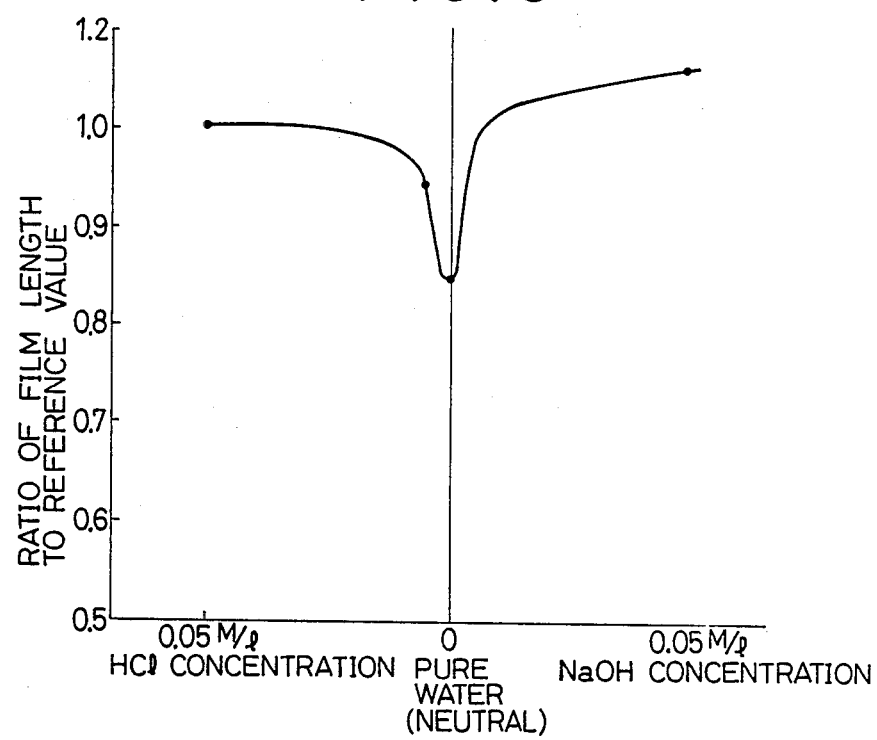
FIG. 3 is a diagram showing the relation between the change in length and the environment obtained of an expansible macromolecular material produced in Example 2.

The relation of the change in length and the environment obtained for this material was as shown in FIG. 3. The relation of the change in length and the environment obtained of this material was as shown in FIG. 3. The results were substantially the same as those obtained in Example 1.

Figure 4:
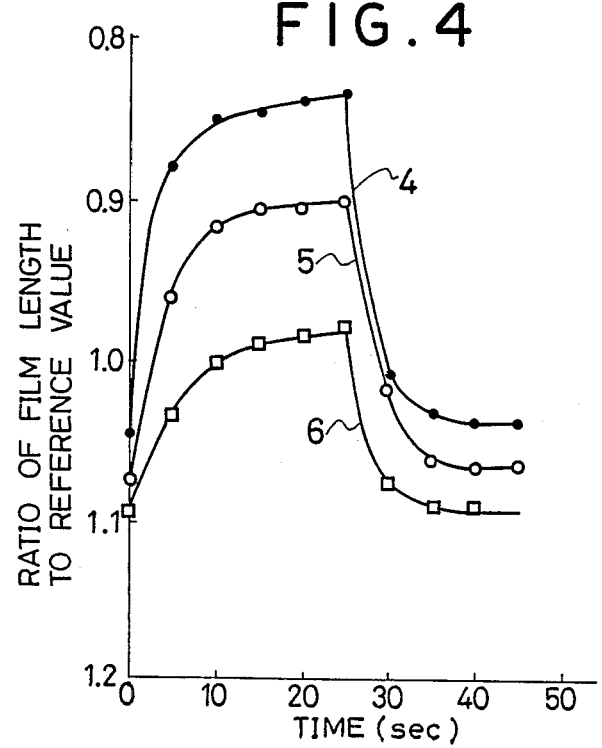
FIG. 4 is a diagram showing the speed of response of the expansible macromolecular material produced in Example 2.

Subsequently, this material was tested for response time by following the procedure of Example 1. The results were as shown in FIG. 4. In the graph, the curves 4, 5, and 6 represent the changes in length over the course of time under tensions of 125 g/cm$^2$, 208 g/cm$^2$, and 292 g/cm$^2$ respectively. It is noted from the graph that the response speed of the material of this example was higher than that of the material of Example 1.

EXAMPLE 3

Figure 5:
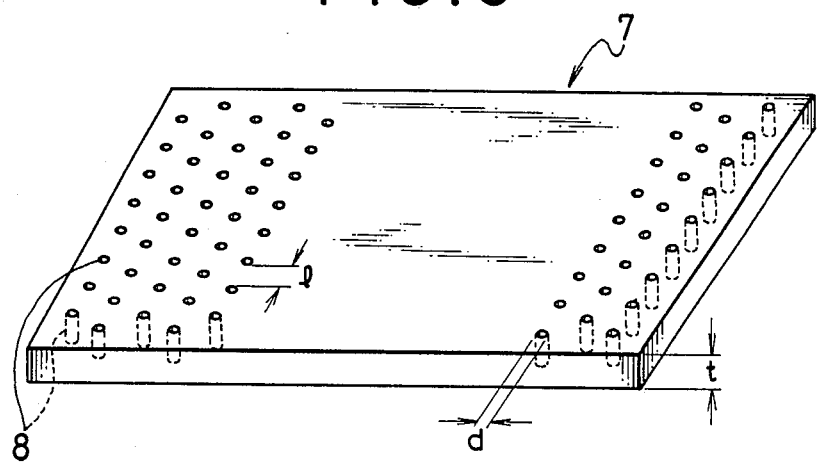
FIG. 5 is an explanatory perspective view of a porous macromolecular membrane described in Example 3.

A porous macromolecular membrane 7 of the present invention illustrated in FIG. 5 will be described below. This porous macromolecular membrane is formed of the aforementioned material for porous macromolecular membrane and possesses the thickness of the material. The thickness of this membrane suitably falls in the range of 10 to 500 μm. In the membrane, numerous holes 8 extending in the direction of thickness are arranged in parallel. The diameter (d) of the holes 8, which is smaller than the thickness of the membrane, suitably falls in the range of 2 to 50 μm.

A porous macromolecular membrane was produced as follows. On a flat glass plate, pin-like projections of a diameter, d, were perpendicularly raised as arranged in parallel to one another and spaced by a fixed interval of l. On the surface of this glass plate, a mixture as the material for a porous macromolecular material was applied in a prescribed thickness in the range of 10 to 500 μm. The layer of the mixture thus formed on the glass plate was subjected to not less than 10 cycles of alternate freezing and defrosting treatments, the freezing treatment being effected at a temperature in the range of −10° C. to −200° C. and the defrosting treatment being effected at normal room temperature, dried in a draft, and finally removed from the surface of the glass plate.

EXAMPLE 4

Figure 6:
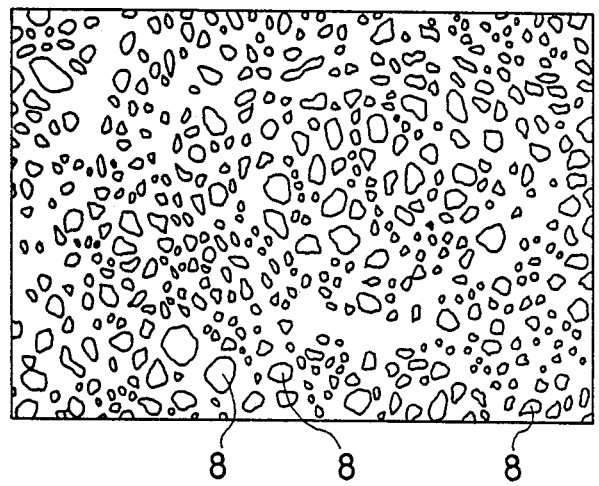
FIG. 6 is a top view of a porous macromolecular membrane described in Example 4.

A porous macromolecular membrane of this invention having irregularly arranged holes 8 formed in the direction of thickness and communicating with each other was prepared. A top view of this membrane is shown in FIG. 6. This membrane permitted quick permeation of a solvent and showed an improved response property.

EXAMPLE 5

Figure 7:
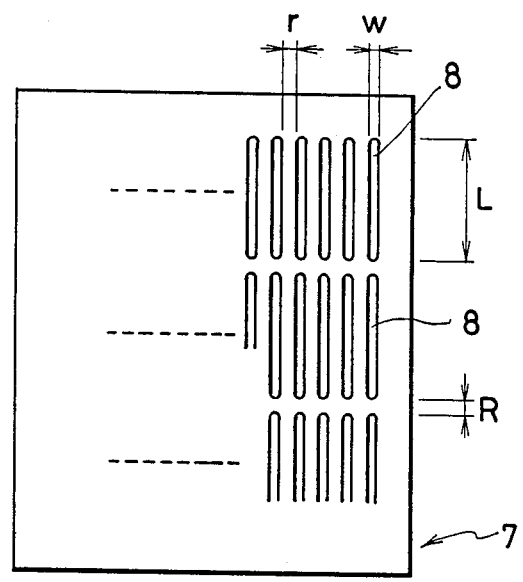
FIG. 7 is a top view of a porous macromolecular membrane described in Example 5.

As compared with the porous macromolecular membrane of Example 3 containing the through holes 8 which had a circular cross section, a porous macromolecular membrane containing through holes having a cross section of the shape of a slit as illustrated in FIG. 7 exhibited a notably increased speed of response.

As illustrated, the holes are desired to have a length, L, in the range of 10 to 500 μm and a width, W, in the range of 5 to 50 μm and to be separated by a lateral interval, r, in the range of 5 to 50 μm and a longitudinal interval, R, in the range of 10 to 100 μm. This macromolecular membrane was produced by following the procedure of Example 3, except that oblong strips conforming to the dimensions of the slit-like holes were used in the place of the aforementioned pin-like projections. Then, the porous macromolecular membrane of W=20 μm, r=20 μm, L=220 μm, and R=30 μm exhibited a response time of 1 second.

What is claimed is:

1. A method for the production of a porous macromolecular material, which comprises:
    (a) forming a composite polymer by mixing an aqueous solution of about 5–30 wt. % of a polyvinyl alcohol having a molecular weight of at least 70,000 and a saponification degree of at least 98% with at least one member selected from the group consisting of an aqueous solution of about 10–50% by weight of an acidic macromolecular electrolyte having a molecular weight of at least 50,000 and an aqueous solution of about 10–50% by weight of a basic macromolecular electrolyte having a molecular weight of at least 50,000 in amounts such that the molar ratio of said polyvinyl alcohol to either of said acidic macromolecular electrolyte and basic macromolecular electrolyte falls within the range of 10 to about 3:2 to about 1;
    (b) subjecting the composite polymer to between 1 and about 20 cycles of alternate freezing and defrosting treatments, said freezing treatment being effected at a temperature in the range of about −10° C. to −200° C., and said defrosting treatment being effected at room temperature;
    (c) elongating said composite polymer;
    (d) subjecting said composite polymer in the elongated state to between 1 and 20 cycles of sequential treatments of elongation, freezing in the elongated state at a temperature in the range of about −15° C. to −200° C., and defrosting in the elongated state at room temperature; and
    (e) drying said composite polymer in a draft.

2. The method of claim 1 which comprises mixing an aqueous solution of 10 to 50 wt. % of a polyvinyl alcohol having a molecular weight of at least 30,000 with an acidic macromolecular electrolyte and a basic macromolecular electrolyte each having a molecular weight of at least 50,000 in amounts such that the molar ratio of the polyvinyl alcohol to either of the acidic and basic macromolecular electrolytes falls in the range of 10 to about 3:2 to about 1, thereby forming a composite polymer and subjecting said composite polymer to between 1 and 20 cycles of alternate freezing and defrosting treatment, said freezing treatment being effected at a temperature in the range of −10° C. to −200° C. and said defrosting treatment being effected at normal room temperature.

3. The method of claim 1, wherein said acidic macromolecular electrolyte is at least one member seleced from the group consisting of polyacrylic acid and polymethacrylic acid.

4. The method of claim 1, wherein said basic macromolecular electrolyte is at least one primary amine.

5. The method of claim 1, wherein said acidic macromolecular electrolyte is at least one member selected from the group consisting of polyacrylic acid and polymethacrylic acid.

6. The method of claim 1, wherein said basic macromolecular electrolyte is at least one primary amine.

* * * * *